United States Patent [19]

Michaelis et al.

[11] Patent Number: 5,919,757
[45] Date of Patent: Jul. 6, 1999

[54] AQUEOUS PHARMACEUTICAL PREPARATIONS OF G-CSF WITH A LONG SHELF LIFE

[75] Inventors: Uwe Michaelis; Rainer Rudolph, both of Weilheim; Gerhard Winter, Dossenheim; Heinrich Woog, Laudenbach, all of Germany

[73] Assignee: Boehringer Mannheim GmbH, Mannheim, Germany

[21] Appl. No.: 08/857,172

[22] Filed: May 15, 1997

Related U.S. Application Data

[63] Continuation of application No. 08/454,184, filed as application No. PCT/EP93/03544, Dec. 15, 1993.

[30] Foreign Application Priority Data

Dec. 18, 1992 [DE] Germany .............................. 42 42 919

[51] Int. Cl.⁶ .................................................. A61K 38/17
[52] U.S. Cl. .................................... 514/8; 514/12; 514/21
[58] Field of Search ..................................... 514/8, 12, 21

[56] References Cited

U.S. PATENT DOCUMENTS 4,992,419 2/1991 Woog et al. ................................ 514/8
5,104,651 4/1992 Boone et al. .......................... 424/85.1

FOREIGN PATENT DOCUMENTS

| 0 373 679 | 6/1990 | European Pat. Off. . |
| 0 306 824 | 6/1992 | European Pat. Off. . |
| 2193631 | 11/1990 | United Kingdom . |
| WO 93/03744 | 3/1993 | WIPO . |
| WO 93/03745 | 3/1993 | WIPO . |

OTHER PUBLICATIONS

M. Oh–eda et al.; "Olinked Sugar Chain of Human Granulocyte Colony–stimulating Factor Protects It against Polymerization and Denaturation Allowing It to Retain Its Biological Activity"; The Journal of Biological Chemistry, vol. 265, No. 20, Jul. 15, 1990, pp. 11432–11435.

The Merck Index, 12$^{th}$ ed., Pub. Merck & Co., Inc. Rahway, NJ, U.S.A. (1996). pp. 627 and 773.

Neupogen® product package insert, Amgen, Nov. 25, 1992.

*Primary Examiner*—Phyllis G. Spivack
*Attorney, Agent, or Firm*—Nikaido Marmelstein Murray & Oram LLP

[57] ABSTRACT

Aqueous pharmaceutical preparations of G-CSF are disclosed that are stable on storage and a buffer selected from the group consisting of a salt of citrate, maleate, a combination of phosphate and citrate, and arginine; and at least one surfactant.

8 Claims, 3 Drawing Sheets

Fig.1

○ ACETEATE 10 mM
■ PHOSPHATE 20 mM
▽ PHOSPHATE/CITRATE 20 mM
● CITRATE 20 mM

○ HAc 10 mM
▽ HAc 20 mM
△ HAc 40 mM
□ NaAc 20 mM
● CITRATE/PHOSPHATE 20 mM
■ PHOSPHATE 20 mM

AQUEOUS PHARMACEUTICAL PREPARATIONS OF G-CSF WITH A LONG SHELF LIFE

This application is a continuation of application Ser. No. 08/454,184 filed Jun. 15, 1995 abandoned, which is a 371 of PCT/EP93/03544 Dec. 15, 1993.

The present invention concerns aqueous pharmaceutical preparations of G-CSF which are stable in storage and contain at least one buffer selected from the group acetic acid, lactic acid, citric acid, maleic acid, phosphoric acid and salts thereof or arginine and its salts at a concentration in each case of up to 100 mmol/l for stabilization.

Various pharmaceutical preparations which contain G-CSF (granulocyte colony stimulating factor) are already known from the state of the art.

A pharmaceutical agent containing G-CSF is described in DE 37 23 781 (GB 2,193,631) which contains at least one pharmaceutically acceptable surface-active agent, saccharide, protein or a high-molecular compound for stabilizing G-CSF. Preparations are proposed which contain human serum albumin as a stabilizing agent. In particular preparations are stated to be advantageous which contain surface-active agents in parts by weight which correspond to 1–10000-fold the amount of G-CSF used.

Stabilized preparations of G-CSF are described in EP 0 373 679 which are characterized essentially by an acidic pH value of the solution, the solutions having as low a conductivity as possible. The solutions have a pH value of 3–3.7 in the case that the solutions contain further pharmaceutical auxiliary substances such as for example buffers or mannitol. If no buffer substances are present in the pharmaceutical formulation, pH ranges of 2.75–4 are described as being advantageous.

Stabilized lyophilisates of human protein preparations are described in EP 0 306 824 in which stabilization is achieved by adding a mixture of urea, amino acids and detergents.

In the earlier PCT Patent Application PCT/EP92/01823 a process is described for the production of well-tolerated pharmaceutical agents containing G-CSF for infusion and injection purposes. The liquid forms of administration are characterized in particular by a low titration acidity and low buffer capacity. The pH values of the described infusion and injection solutions containing G-CSF are in an acidic range of 3.8–4.5.

Processes for the production of liquid forms of pharmaceutical agents containing G-CSF which additionally contain preservatives are known from PCT/EP92/01822. The pH values of the pharmaceutical solutions are in the acidic range of 2.5–4.5. In this case the stabilization of G-CSF is essentially achieved by setting an acidic pH value which is favourable for G-CSF and by adding a mixture of various amino acids.

The previously known pharmaceutical formulations for G-CSF do, however, have some disadvantages. The preparations described in DE 37 23 781 contain pharmaceutical additives or auxiliary substances which, from a medical point of view, cannot simply be judged as harmless. Polymers and proteins have a certain residual risk with regard to their suitability as pharmaceutical additives due to their origin and their physicochemical properties. Proteins of human or animal origin as well as proteins obtained from cell cultures bear a potential residual risk of viral contaminations. Other protein-like impurities which are analytically difficult to detect can also cause immunological reactions in humans due to their antigenic properties. Moreover proteins of animal origin can generally trigger immunological reactions in humans due to their species-specific properties. Long-term reactions after a later re-administration of such proteins are also possible.

The addition of high-molecular compounds may also be problematic. Polymers may accumulate in the body due to their large molecular mass and can thus remain in the body over a long period if no biodegradation occurs. This is a particular risk in the case of subcutaneous administration since removal and distribution via the blood stream is considerably slower compared to intravenous administration. Polymers may also have antigenic properties depending on their molecular mass. In addition the purity of polymers is difficult to guarantee because of the catalysts used for their production or the presence of monomers and other polymer fragments. The use of polymers in liquid pharmaceutical forms of administration should thus be avoided if possible in particular in the case of forms of pharmaceutical agents that can be administered subcutaneously.

The amounts of surfactant described in DE 37 23 781 must also be regarded as problematic from a medical point of view. Here surfactant concentrations are described as being advantageous in which 110000 parts by weight of a surface-active agent are present in relation to the proportion by weight of G-CSF. If on the other hand one considers the preferred application concentrations of G CSF for clinical use of 0.05–1.5 mg/ml in the final pharmaceutical formulations, then this results in correspondingly high surfactant concentrations. These should be avoided from a medical point of view since they can cause local irritations.

A disadvantage of the formulations described above is that, particularly in the case of subcutaneous administration, they lead to local intolerances in the patients due to the low pH value used. The product obtained can cause pain and local tissue irritation in sensitive patients since the physiological pH range of 7.0–7.5 present in tissue is not adhered to.

In addition it is known from the literature that especially non-glycosylated forms of G-CSF are particularly unstable compared to glycosylated G-CSF which is obtained from CHO cells (J. Biol. Chem. 1990, 265, 11432). The stabilization of non-glycosylated forms of G-CSF is therefore particularly difficult and requires specially selected measures in order to formulate this molecule in a stable pharmaceutical formulation.

In addition a major disadvantage of liquid pharmaceutical preparations containing G-CSF was found to be that they tend to relatively easily form turbidities, above all during longer storage or during transport on the distribution channels. In addition it has turned out that the ready-to-administer solutions are very sensitive towards mechanical stress. Mechanical stresses such as for example shaking the solution can influence the liquid pharmaceutical preparations during transport in a diverse and uncontrollable manner. Also incorrect handling and thus possibly mechanical stresses on the pharmaceutical solutions filled into ampoules or vials cannot be absolutely excluded during use by the doctor, medical personnel or the patients. Accordingly robustness towards mechanical stress is a quality criterium for pharmaceutical agents containing protein. Measures to maintain the stability of G-CSF towards mechanical stress have previously not been described in the literature. Although liquid preparations of G-CSF prepared according to conventional processes have an adequate stability even when stored at increased temperatures, the stability of such formulations towards mechanical stress is not satisfactory in all cases. In particular visible turbidities often occur in the pharmaceutical solutions which are caused by the formation of dimers or aggregates of G-CSF. Such changes in the liquid pharmaceutical preparations have, above all, a detrimental effect on the amount of active substance contained in the individual forms of administration and should be avoided as far as possible from a medical point of view.

The object of the present invention was to provide a stable liquid pharmaceutical preparation of G-CSF which enables a proper use of G-CSF as a pharmaceutical agent and which does not have the disadvantages of the previously known pharmaceutical preparations described above. In particular the pharmaceutical preparation should have a long shelf-life, be stable towards mechanical stress, be physiologically well-tolerated, simple to use and be possible to dose precisely. In particular it should have a physiologically compatible pH value.

Surprisingly it was found that stable aqueous pharmaceutical preparations can be produced within the sense of the present invention when a buffer substance selected from the group acetate, lactate, citrate, maleate or phosphate is used as an additive. These are preferably used in such an amount that the concentration of the buffer substance selected in each case is from 2 to 100 mmol/l in the ready-to-administer pharmaceutical preparation which comes on the market. Surprisingly the solutions produced in this manner are substantially stable towards mechanical stress. In addition they have the advantage that, through the selection made of the buffer substances, solutions can be provided which have an advantageous pH value of 4–5 or 7–8 whereas the solutions known from the state of the art preferably require solutions with a pH value of 2.5–3.5 for stabilizing the protein.

An additional advantage of the preparations produced according to the invention is that they are free from protein-like or polymeric auxiliary substances the use of which may be problematic from a medical point of view. Due to the fact that liquid pharmaceutical preparations containing G-CSF can now be produced with a pH value of 7–8, i.e. with a pH value near to the pH value of blood (pH 7.2–7.4), they also have the advantage of being well tolerated and capable of administration substantially free of pain.

A further advantage is that due to the selection made of auxiliary substances, the relatively high amounts of surfactant previously required in the liquid pharmaceutical preparations are no longer necessary. On the contrary low amounts of surfactant of 0.5 mg/ml or less, preferably of 0.01–0.1 mg/ml, are adequate to stabilize G-CSF. Surfactant concentrations (mg/ml) can be used advantageously which are smaller than or at most the same as the amount of G-CSF protein used per unit of volume (mg/ml). This is a particular advantage for those liquid pharmaceutical preparations which are intended for the subcutaneous administration of G-CSF. In addition the measures according to the invention lead to an adequate stabilization for pharmaceutical preparations of the labile non-glycosylated G-CSF molecules in particular. The specific selection of the auxiliary substances provides pharmaceutical preparations containing G-CSF which are overall very well tolerated and which represent qualitatively high-grade preparations with regard to protein stability.

DESCRIPTION OF THE PREFERRED EMBODIMENTS

The pharmaceutical preparations containing G-CSF according to the invention contain the active substance in an amount which is adequate to achieve a therapeutic effect. Usually concentrations of active substance of 0.01–5 mg/ml are used, preferably 0.1–1.5 mg/ml.

Acetic acid, citric acid, lactic acid, maleic acid and phosphoric acid or physiologically tolerated salts thereof are used according to the invention as pharmaceutical auxiliary substances and buffer substances. In the production of the auxiliary substance solution these buffer substances can either be present in the form of the corresponding free acid or in the form of the alkali, alkaline-earth or ammonium salts. The solution can in addition contain further common pharmaceutical auxiliary substances. The sequence of addition of the various auxiliary substances or of the active substance during the production of the liquid pharmaceutical preparations is largely independent of the stabilizing effect in storage found according to the invention and is at the discretion of the person skilled in the art. The desired pH value of the solution is adjusted by adding bases such as alkali hydroxides, alkaline-earth hydroxides or ammonium hydroxide. Sodium hydroxide is preferably used for this. The adjustment of the desired pH value can in principle be achieved by adding basic solutions. In general salts of strong bases with weak acids come into consideration for this such as e.g. sodium acetate, sodium citrate, di-sodium or di-potassium hydrogen phosphate or sodium carbonate. If the pharmaceutical solution of auxiliary substance has a basic pH value, it is adjusted by titration with an acid until the desired pH range of 4–5 or 7–8 is reached. Physiologically tolerated inorganic or organic acids come into consideration as acids such as for example hydrochloric acid, phosphoric acid, acetic acid, citric acid or conventional solutions of substances which have an acidic pH value. In this respect preferred substances are salts of strong acids with weak bases such as e.g. sodium dihydrogen phosphate or potassium dihydrogen phosphate.

Arginine and salts thereof are also used according to the invention as pharmaceutical auxiliary substances and buffer substances.

The concentrations of the buffer substances acetic acid, citric acid, lactic acid, maleic acid or phosphoric acid in the ready-to-administer liquid pharmaceutical preparation are preferably about 2–100 mmol/l in each case. Due to the fact that the aforementioned acids are usually used in the form of their salts during the production of the pharmaceutical auxiliary substance solution and less frequently in the form of their free acids, reference is made in the following in each case to the anion concentrations of these acids for the sake of simplicity i.e. for example acetate, citrate, lactate, maleate or phosphate. The total concentrations of buffer substances should not exceed a value of 100 mmol/l, preferably 80 mol/l. The total concentration of the buffer substances is preferably about 5–40 mmol/l.

It has turned out that particular pH ranges of the liquid pharmaceutical preparation in combination with particular buffer substances result in particularly stable solutions. When an acetate or lactate buffer is used at a concentration of 5–40 mmol/l and the pH value of the solution is adjusted to a range of about 2–5, a pharmaceutical preparation that is particuarly stable towards mechanical stress is obtained. The following buffer concentrations and pH values are preferably used: 5–80 mmol/l, in particular 10–30 mmol/l, acetate or lactate and pH 3.5–5.

Citrate is used at a concentration of 5–40 mmol/l, preferably 5–20 mmol/l. A combination of the buffer substances citrate and phosphate is preferably used in which case the total concentration of the buffer substances is 10–40 mmol/l, preferably 15–30 mmol/l. The pH values of liquid pharmaceutical preparation are preferably in the range of about 2.5–3.5 or 7–7.5.

Maleate is preferably used at a concentration of 5–40 mmol/l. The pH values of the liquid pharmaceutical preparation in this case are preferably in the range of about 2.5–3.5 or 7–7.5.

Phosphate is used at a concentration of 5–80 mmol/l, preferably of 5–30 mmol/l, alone or in combination with one of the other buffer substances. The pH values of the liquid pharmaceutical preparation which only contains phosphate buffer are preferably in the range of about 3.5–5 or 7–8.

Arginine phosphate, arginine chloride and arginine citrate buffer is also used at a concentration of 2–100 mmol/l, preferably 5–80 mmol/l. The pH value of the liquid preparation containing arginine buffer is about 7–8, preferably 7–7.5.

The described selection of buffer systems according to the invention at physiologically tolerated pH values and physiologically tolerated concentrations is also a good idea and advantageous in the case of solutions of G-CSF prepared from lyophilisates or powders by redissolving.

Since mechanical agitation (shaking) is exerted when lyophilisates are redissolved it is important in this case to specifically select particular buffer systems and pH values. Selection of buffer systems or pH values that are not within the scope of the invention can lead to the formation of aggregates, turbidities and thus to a low quality product.

In this connection it is up to the person skilled in the art whether the acids, salts, bases required to produce the pH values and buffer systems according to the invention are contained in a lyophilisate or in the aqueous solution used for dissolving or in both components.

The aqueous preparations according to the invention can be used to produce lyophilisates by conventional lyophilization or powders by for example spray drying. The preparations according to the invention are obtained again by dissolving these in water or aqueous solutions. It has turned out that redissolved lyophilisates which contain arginine buffer in a pH range of 7–7.5 are stable for at least 24 hours.

The stabilization of G-CSF molecules which is possible by means of the said buffer substances relates in principle to all G-CSF molecules produced by recombinant processes and variants thereof. The term G-CSF or G-CSF variant according to the present invention includes all naturally occurring variants of G-CSF as well as G-CSF proteins modified by recombinant DNA technology that are derived therefrom, in particular fusion proteins which additionally contain other protein sequences in addition to the G-CSF part. In this regard a G-CSF mutein is particularly preferred with a N-terminal Met residue at position −1 which is suitable for expression in prokaryotic cells. A recombinant methionine-free G-CSF variant which can be produced according to PCT/EP91/00192 is equally suitable. The term "G-CSF variant" is understood to include those G-CSF molecules in which one or several amino acids may be deleted or replaced by other amino acids wherein the essential properties of G-CSF are substantially retained. Suitable G-CSF muteins are described for example in EP 0 456 200.

Measurement of the turbidity of solutions containing G-CSF is particularly suitable for testing the stability of liquid pharmaceutical preparations towards mechanical stress. The evaluation of the turbidity of a protein solution after being subjected to mechanical stress is particularly valuable as a test method which is simple to carry out. The occurrence of turbidities correlates with the formation of polymers, oligomers and aggregates. The optical assessment proves to be superior in some cases to more special methods for detecting dimers and aggregates (e.g. HPLC methods) since in the case of the turbidity method large aggregates are not removed from the quanitification by sample preparation as is required for example in the case of HPLC but instead are assessed in the original vessel and can thus be reliably detected. The quantification of turbidity phenomena can easily be carried out with commercial turbidimeters, scattered light photometers etc. The evaluation of such results can also be translated into the requirements of pharmacopeias which for example define bench marks for turbidity below which solutions can be regarded as being clear or slightly turbid.

It is expedient to add auxiliary substances which act isotonically for the production of well-tolerated parenteral pharmaceutical preparations if isotonicity cannot be already achieved by the osmotic properties of the active substance and the auxiliary substances used for stabilization. For this purpose non-ionized, well-tolerated auxiliary substances such as e.g. mannitol, glycerol or other sugar alcohols are mainly used.

In the case of G-CSF, mannitol is preferably used without this being important for the stability of G-CSF. The protein is equally stable in mannitol-free preparations, but these solutions are less well tolerated due to their lack of isotonicity.

It is not advantageous to add salts to adjust the isotonicity, since high concentrations of salts or ions promote the formation of G-CSF aggregates. Therefore salts are advantageously added in small amounts. The buffer concentrations are calculated so that the pH-stabilizing effect is achieved but the ionic strength is kept as small as possible. The buffer concentrations are preferably in the range of up to 80 mmol/l, particularly preferably of less than 30 mmol/l.

The ready-to-administer injection solutions can also contain further convential auxiliary substances or additives. Antioxidants such as for example glutathione, ascorbic acid or similar substances, chaotropic auxiliary substances such as for example urea and amino acids such as for example arginine, lysine, ornithine etc. can be added.

The invention is described in more detail in the following on the basis of representative examples of embodiments:

EXAMPLE 1
General Procedure for Producing the Liquid Pharmaceutical Preparations The solutions of G-CSF used in the examples were prepared by dissolving the described auxiliary substances in water for injection purposes, adding G-CSF in the stated amount and if necessary adjusting the pH value with a small amount of buffer component to exactly the target value. The solutions were then filtered through a suitable sterilized membrane filter of 0.2 μm pore size and filled into injection vials made of glass of hydrolytic class I and closed with sterile, teflonized rubber stoppers. The filling is preferably carried out under a nitrogen atmosphere.

EXAMPLE 2
Test Methods for the Stability Determination

The closed and flanged vials were stored in the dark at defined storage temperatures and subsequently examined with reversed phase HPLC (RP-HPLC), gel chromatography or size exclusion chromatography (SEC HPLC) and Western blot for protein purity as well as for the occurrence of aggregates and dimers. The methods used can be described as follows:

2.1 Reversed phase HPLC

The RP-HPLC was carried out using a Nucleosil C18 column (Knauer Company). The mobile phase consisted of 0.12% (v/v) trifluoroacetic acid (TFA)/water (A) and 0.1% (v/v) TFA/acetonitrile (B). The chromatography was carried out at a flow rate of 0.5 ml/min using a linear gradient of A to B.

The injection amount was 3–6 µg G-CSF depending on the formulation. It was evaluated at a wavelength of 214 nm by means of the peak area using an external standard.

2.2 Size exclusion chromatography (SEC)

A TSK G 2000 SW separation column (7.5×300 mm) was used for the SE chromatography. The separations were carried out isocratically at room temperature and a flow rate of 0.6 ml/min in a phosphate buffer (22.2 mM $Na_2HPO_4$; 107.7 mM $KH_2PO_4$; pH 6.2). The injection amount was 3–6 µg G-CSF. It was evaluated at a detection wavelength of 214 nm by means of the peak area using an external standard.

2.3 SDS page/Western blot

3 µg rhG-CSF is applied under non-reducing conditions to a 12 per cent polyacrylamide SDS gel and subjected to gel electrophoresis. Subsequently the G-CSF monomers, dimers or aggregates separated according to their molecular weight are transferred by electro-blotting onto nitrocellulose. The protein bands are identified by incubation with a specific polyclonal biotinylated anti-G-CSF antibody (PAB<GCSF>IgG) and detected by means of the phosphatase technique using streptavidin-alkaline phosphatase conjugate (SA-AP conjugate), 5-bromo-4-chloro-3-indolyl phosphate (BCIP) and nitro blue tetrazolium (NBT).

The percentage amounts of monomers, dimers and aggregates are determined by laser densitometric evaluation with the aid of a series of rhG-CSF standards.

2.4 NFS-60 bioassay (biological activity)

The in vitro determination of the G-CSF activity is based on the measurement of cell counts in a cell culture of NFS-60 cells stimulated by G-CSF.

Under suitable conditions it is possible to correlate the dehydrogenase activity of the cells with the concentration of G-CSF in the medium. Suitable dilutions of the G-CSF buffer solution are prepared in order to obtain a readily measurable increase in the dehydrogenase activity.

The activity is then measured photometrically at 570 and 690 nm; the reduction of the tetrazolium salt MTT (yellow) to formazan (blue) is measured.

The in vitro activity of G-CSF is calculated by comparing the data for the sample with those for the standard according to the parallel line method. It is evaluated according to the requirements of Ph. Eur. (VIII, 13).

2.5 Photometry OD 280 (protein content)

The G-CSF UV spectrum has an absorbance maximum at 280 nm which is due to side chain chromophores such as tryptophan, tyrosine and phenylalanine residues. The measurement is carried out in comparison to placebo solutions by means of a:

UV spectrophotometer (e.g. Uvikon 810 P or 941, Kontron Instruments)

Semi-micro quartz cuvettes, 500 µl, path length: 1 cm (e.g. Hellma, Suprasil, Cat. No. 104.002B-QS)

2.6 Scattered light measurement, turbidity measurement

The measurement is carried out directly on the undiluted product solution in glass cuvettes (diameter 2 cm). The scattered light that is diffusely deflected by the liquid is measured at an angle of 90 degrees. It is measured in comparison to formazine standard suspensions according to DIN 38404C2, the values are stated in TU/F. The measurement is carried out on a suitable turbidity photometer, e.g. LTP 5 (Dr. Lange Company, Düsseldorf).

EXAMPLE 3

Investigations on the Mechanical Stress Capacity (turbidity)

G-CSF solutions at a concentration of 0.5 mg/1 ml were prepared by dialysis with the buffers mentioned in the following. In order to determine turbidities occurring after mechanical stress, samples of 1 ml in each case were dispensed into injection bottles made of glass of hydrolytic class I and closed with stoppers. The samples were treated on laboratory shaking machines (e.g. Heidolph Company) for 10 seconds at maximum intensity. Immediately after the mechanical stress process, the scattered light measurement was carried out using a Hitachi F4000 fluorescence spectrophotometer at an EX and EM wavelength of 360 nm in each case. In the following the scattered light intensities at 360 nm are given in relation to the pH value and to the buffer used. The stated molarities of the acetate and citrate buffer relate to the molarities used of acetic acid and citric acid. The appropriate pH values were adjusted with sodium hydroxide solution. Phosphate/citrate buffer was prepared by adding the appropriate amount of citric acid and adjusting the pH with disodium hydrogen phosphate. Phosphate buffer was prepared by adding the given molarities of sodium hydrogen phosphate and adjusting the pH values with phosphoric acid or disodium hydrogen phosphate.

EXAMPLE 4

A liquid pharmaceutical preparation of G-CSF is prepared as stated in example 1 and the pH value of the solution is adjusted to 4.5. The preparations contained the components stated in Table 1:

TABLE 1

| | G-CSF solutions with a pH of 4.5 | | | |
|---|---|---|---|---|
| | Formulation 1 | Formulation 2 | Formulation 3 | Formulation 4 |
| G-CSF | 0.25 mg | 0.25 mg | 0.25 mg | 0.25 mg |
| mannitol | 25 mg | 25 mg | — | 25 mg |
| polysorbate 80 | 0.02 mg | 0.02 mg | 0.02 mg | 0.02 mg |
| buffer | citrate/phosphate 5 mmol/l | phosphate 5 mmol/l | phosphate 5 mmol/l | acetate 10 mmol/l |
| water | up to 0.5 ml | up to 0.5 ml | up to 0.5 ml | up to 0.5 ml |
| pH | 4.5 | 4.5 | 4.5 | 4.5 | a) Results with regard to protein purity with stationary storage

Analyses of the liquid formulations 1–4 by RP HPLC, SEC HPLC and Western blot show that the purity of the unchanged protein is >99% and that no dimers or aggregates of G-CSF are detectable. These results were obtained after storing formulations 1–4 for six months at 4–8° C., after storage for four weeks at +30° C. and after storage for four weeks at +40° C. The results show that solutions of G-CSF at a pH of 4.5 and under various storage conditions can be characterized as being substantially stable with regard to stationary storage conditions.

b) Results with regard to protein purity after mechanical stress

The selection of a buffer and suitable pH value of the solution for physiochemical stability when stored at rest is, however, different with regard to stability after mechanical stress. This stability is achieved at pH 4.5 in acetate and phosphate buffers but not in a buffer mixture of citrate/phosphate. The individual results obtained are shown in the following table:

TABLE 2

|  | Turbidity after 6 months at 4–8° C. | Turbidity after mechanical stress directly after production | at 4–8° C. | at 40° C. |
| --- | --- | --- | --- | --- |
| Formul. 1 | none | strong | strong | strong |
| Formul. 2 | none | none | none | none |
| Formul. 3 | none | none | none | none |
| Formul. 4 | none | none | none | none |

EXAMPLE 5

Figure 1:
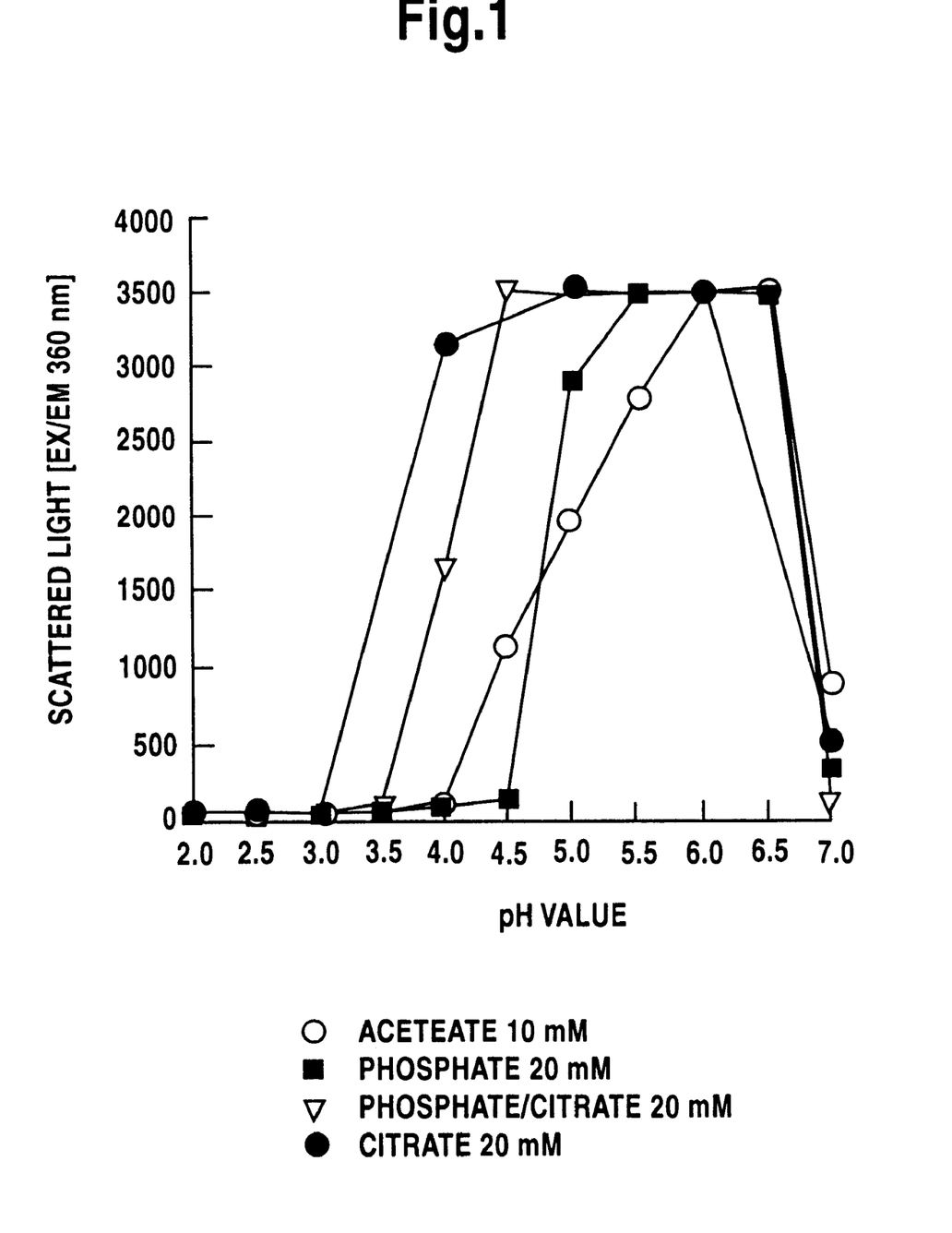
FIGS. 1–4 show the scattered light measured in relation to the pH value of several solutions prepared in accordance with the invention, after mechanical stress was induced.
Figure 2:
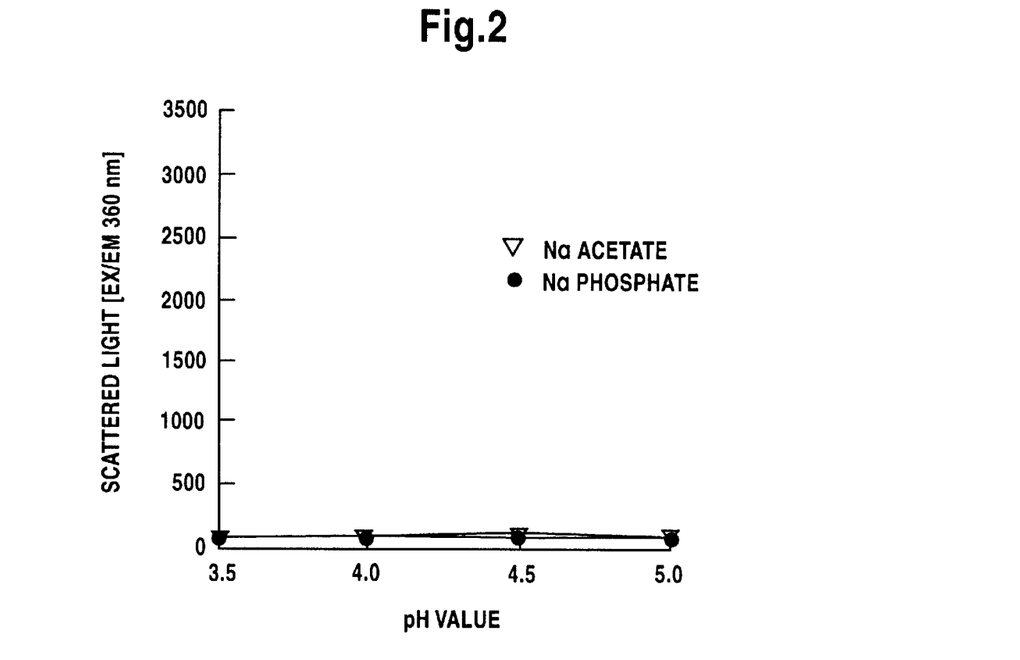
Figure 3:
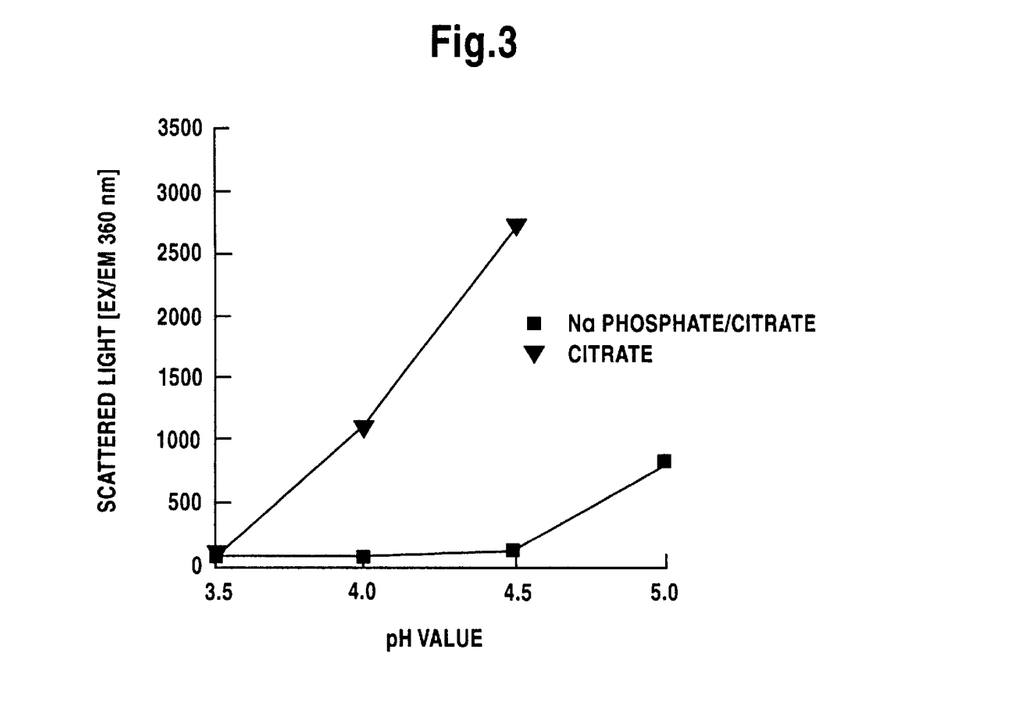
Figure 4:
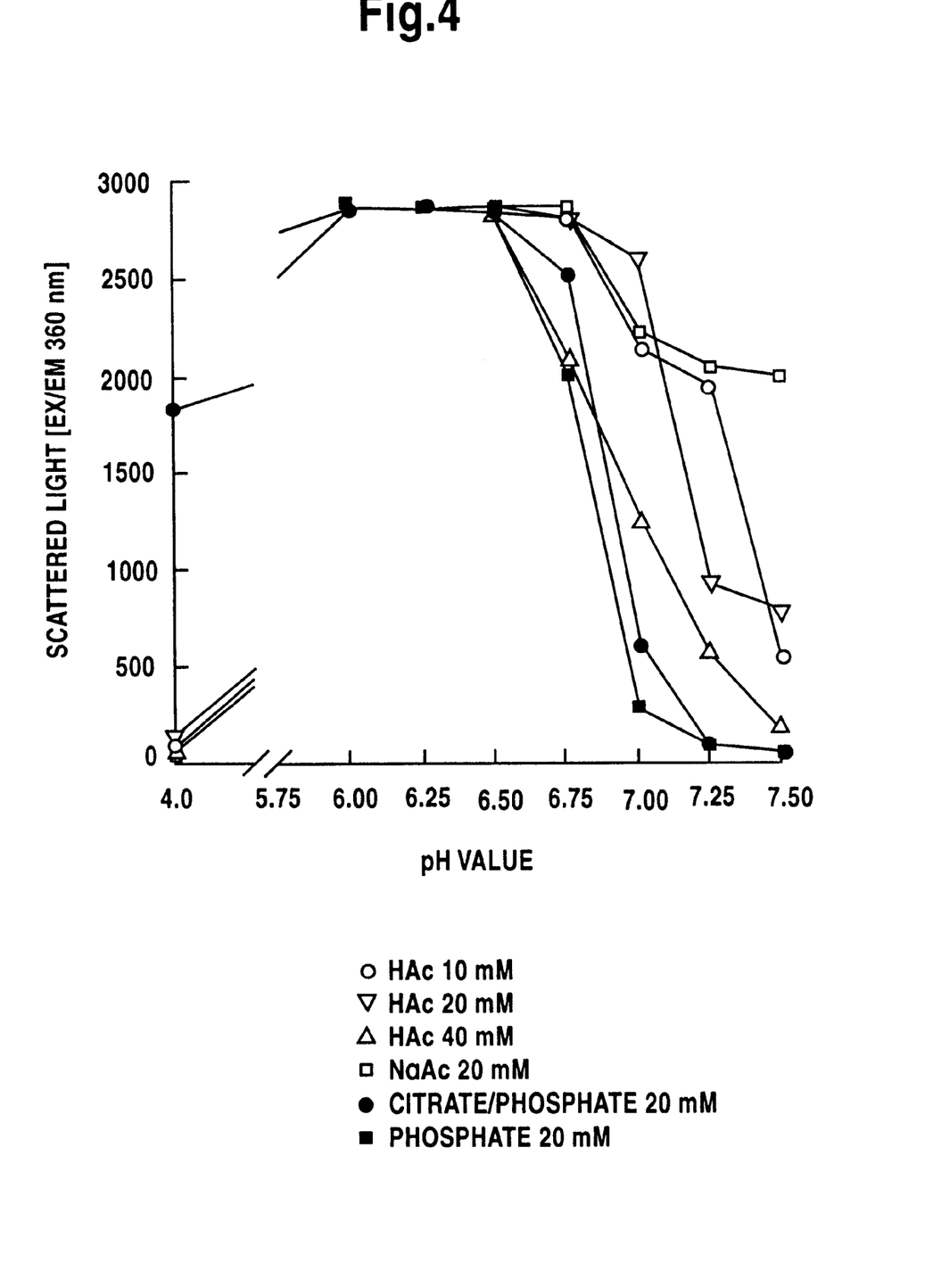

Solutions of G-CSF containing various buffer systems and 0.005% (0.05% in FIGS. 2 and 3) polysorbate 80 in each case were prepared as described in example 3. Various solutions which different pH values between 2–7.5 at intervals of 0.5 pH units were prepared for each buffer system examined (i.e. 13 solutions per buffer system). The mechanical stress resistance of the solutions was examined by the methods described above (example 3) using scattered light measurements. The following buffer systems were examined (content of G-CSF and other auxiliary substances as in example 3):

5.1 Acetate 10 mmol/l 5.2 Acetate 20 mmol/l 5.3 Acetate 40 mmol/l 5.4 Phosphate 20 mmol/l 5.5 Phosphate/citrate total 20 mmol/l, containing 10 mmol/l phosphate 5.6 Lactate 10 mmol/l 5.7 Maleate 10 mmol/l 5.8 Citrate 20 mmol/l The scattered light was measured in relation to the pH value of the solution after the mechanical stress was completed. The results are shown in FIGS. 1–4. These show the individual shape of the pH turbidity curve for each buffer system. Citrate is particularly unsuitable in the pH range of 4–6.5; citrate/phosphate buffer is unsuitable in a pH range of 4.5–6.5; acetate is unsuitable in the pH range of about 5–7 and phosphate is unsuitable in a pH range of about 5–6.75. Lactate behaves like acetate, maleate and citrate/phosphate.

EXAMPLE 6

Investigations of the Mechanical Stability of G-CSF Solutions at a Concentration of 0.35 mg/ml Containing 0.5 mg/ml Tween 80 in Relation to the Buffer Concentration and pH Value G-CSF solutions at a concentration of ca. 5 mg/ml were diluted with the buffer solutions described below to a content of active substance of 0.35 mg/ml. All buffer solutions contained 0.05% polysorbate 80. The buffer solutions were prepared by firstly adding the respective basic salt components in the stated molar concentration and adjusting the pH value to the stated value using the corresponding acid. The G-CSF buffer solutions obtained in this manner were dispensed in an amount of 10 ml into injection bottles made of glass of hydrolytic class 1, closed with a suitable stopper and shaken for 10 seconds at maximum intensity on a laboratory shaking apparatus (e.g. Heidolph Company). After a standing time of ca. 10 minutes a turbidity value (TU/F) calibrated against a formazine standard (German Pharmacopeia) was determined with a LTP 5 scattered light photometer (measuring angle 90°) of the Dr. Lange Company.

TABLE 3a

Turbidity of the unshaken solution

|  |  | Acetate buffer TU/F | Phosphate buffer TU/F | Citrate buffer TU/F |
| --- | --- | --- | --- | --- |
| 80 mmol | pH 7.5 | 0.56 | 0.58 | 0.51 |
|  | pH 7 | 0.47 | 0.51 | 0.43 |
|  | pH 5 | 0.55 | 0.47 | 0.48 |
|  | pH 4.5 | 0.36 | 0.47 | 0.46 |
|  | pH 4 | 0.39 | 0.46 | 0.41 |
|  | pH 3.5 | 0.3 | 0.54 | 0.41 |
| 40 mmol | pH 7.5 | 0.57 | 0.4 | 0.45 |
|  | pH 7 | 0.51 | 0.37 | 0.39 |
|  | pH 5 | 0.62 | 0.4 | 0.48 |
|  | pH 4.5 | 0.42 | 0.58 | 0.52 |
|  | pH 4 | 0.44 | 0.41 | 0.55 |
|  | pH 3.5 | 0.42 | 0.43 | 0.37 |
| 20 mmol | pH 7.5 | 0.65 | 0.39 | 0.4 |
|  | pH 7 | 0.8 | 0.46 | 0.4 |
|  | pH 5 | 0.62 | 0.49 | 0.39 |
|  | pH 4.5 | 0.47 | 0.42 | 0.39 |
|  | pH 4 | 0.44 | 0.43 | 0.47 |
|  | pH 3.5 | 0.49 | 0.37 | 0.38 |
| 10 mmol | pH 7.5 | 0.54 | 0.43 | 0.55 |
|  | pH 7 | 0.68 | 0.38 | 0.49 |
|  | pH 5 | 0.42 | 0.41 | 0.55 |
|  | pH 4.5 | 0.37 | 0.45 | 0.43 |
|  | pH 4 | 0.35 | 0.36 | 0.44 |
|  | pH 3.5 | 0.4 | 0.43 | 0.42 |
| 5 mmol | pH 7.5 | 0.83 | 0.57 | 0.35 |
|  | pH 7 | 0.63 | 0.37 | 0.37 |
|  | pH 5 | 0.65 | 0.41 | 0.42 |
|  | pH 4.5 | 0.42 | 0.4 | 0.31 |
|  | pH 4 | 0.4 | 0.4 | 0.64 |
|  | pH 3.5 | 0.38 | 0.48 | 0.44 |

TABLE 3b

Turbidity of the shaken solution

|  |  | Acetate buffer TU/F | Phosphate buffer TU/F | Citrate buffer TU/F |
| --- | --- | --- | --- | --- |
| 80 mmol | pH 7.5 | 1.49 | 0.74 | 0.8 |
|  | pH 7 | 1.94 | 0.77 | 0.79 |
|  | pH 5 | 0.73 | 0.75 | 2.8 |
|  | pH 4.5 | 0.42 | 0.68 | 2.1 |
|  | pH 4 | 0.45 | 0.57 | 0.81 |
|  | pH 3.5 | 0.32 | 0.66 | 0.57 |
| 40 mmol | pH 7.5 | 1.52 | 0.7 | 0.74 |
|  | pH 7 | 1.24 | 0.58 | 0.57 |
|  | pH 5 | 0.8 | 0.6 | 1.69 |
|  | pH 4.5 | 0.5 | 0.64 | 0.89 |
|  | pH 4 | 0.63 | 0.62 | 0.89 |
|  | pH 3.5 | 0.55 | 0.64 | 0.47 |
| 20 mmol | pH 7.5 | 2.2 | 0.45 | 0.57 |
|  | pH 7 | 2.9 | 0.6 | 0.57 |
|  | pH 5 | 0.7 | 0.77 | 0.95 |
|  | pH 4.5 | 0.55 | 0.48 | 0.6 |
|  | pH 4 | 0.56 | 0.5 | 0.74 |
|  | pH 3.5 | 0.43 | 0.4 | 0.55 |
| 10 mmol | pH 7.5 | 1.22 | 0.59 | 0.75 |
|  | pH 7 | 1.4 | 0.46 | 0.65 |
|  | pH 5 | 0.47 | 0.51 | 1.35 |
|  | pH 4.5 | 0.43 | 0.45 | 0.59 |
|  | pH 4 | 0.47 | 0.38 | 0.58 |
|  | pH 3.5 | 0.44 | 0.51 | 0.46 |
| 5 mmol | pH 7.5 | 2 | 0.76 | 0.48 |
|  | pH 7 | 1.4 | 0.6 | 0.69 |
|  | pH 5 | 0.47 | 0.51 | 0.69 |
|  | pH 4.5 | 0.43 | 0.44 | 0.44 |
|  | pH 4 | 0.47 | 0.44 | 0.81 |
|  | pH 3.5 | 0.44 | 0.5 | 0.44 |

The data show that phosphate buffers in the examined pH range exhibit low values for turbidity over the entire molarity of 5–80 mmol/l which increase slightly under mechanical stress.

Acetate buffers exhibit very low values for turbidity in the pH range of 3.5–4.5 even under mechanical stress.

Citrate buffers at concentrations of 5–40 mmol/l are suitable for stabilization in the pH range of 7–7.5.

EXAMPLE 7

Liquid formulations are described in a pH range of 7.0–7.5 to some of which further auxiliary substances from the group of antioxidants and chaotropic auxiliary substances are added in addition to isotonizing additives.

In order to prepare the formulations mentioned below, the appropriate auxiliary substances were dissolved in water for injection purposes, G-CSF was added and if necessary the pH value was adjusted exactly by small amounts of the appropriate buffer components. The solutions were sterilized by filtration through a sterilized membrane filter with a pore size of 0.2 μm and dispensed under aseptic conditions into sterile injection bottles made of glass of hydrolytic class 1 and closed with sterile, teflonized rubber stoppers. The dispensing was carried out under a nitrogen atmosphere. The flanged injection bottles were stored in the dark at defined storage temperatures until the examination. The methods described in examples 2 and 3 were used for the examination.

TABLE 4a

Liquid G-CSF preparation; pH 7

|  | Formulation 5 | Formulation 6 | Formulation 7 |
| --- | --- | --- | --- |
| G-CSF | 0.35 mg | 0.35 mg | 0.35 mg |
| Polysorbate | 0.1 mg | 0.1 mg | 0.1 mg |
| Mannitol | 40 mg | 40 mg | 40 mg |
| Buffer | $Na_2HPO_4 12H_2O$ 1.5 mg | $Na_2HPO_4 12H_2O$ 1.5 mg | $Na_2HPO_4 12H_2O$ 1.5 mg |
| Glutathione | — | 0.5 mg | — |
| Urea | — | — | 5 mg |
| Water for injection purposes | up to 1 ml | up to 1 ml | up to 1 ml |

TABLE 4b

Analytical data for G-CSF liquid formulations at pH 7

|  | Storage for 4 weeks at 4–8° C. | | |
| --- | --- | --- | --- |
|  | I | II | III |
| Formulation 5 | >99% | >99% | 2.7% |
| Formulation 6 | 99% | >99% | 4.8% |
| Formulation 7 | >99% | >99% | 0.6% |

I Purity of the unchanged protein in RP HPLC
II Purity of the unchanged protein in SEC HPLC
III Dimers/aggregates in Western blot The analytical data in Table 4b show that stable solutions are obtained at pH 7 and the stated phosphate buffer concentration and that the purity of the protein after a four week storage remains largely unchanged (>99%).

EXAMPLE 8

Solutions of G-CSF are prepared in which one solution contains phosphate buffer and has a pH value of 4.5 according to the invention (formulation 8). A second solution is prepared for purposes of comparison which has a pH value of 6.5 (formulation 9).

In order to prepare the medicinal substance solutions, the auxiliary substances were dissolved in water for injection purposes and then G-CSF was added. The solutions were sterilized by filtration through a sterile 0.2 μm membrane filter, dispensed into vials of hydrolytic class I and these were closed with a teflon stopper. Afterwards they were treated for 10 minutes with a laboratory shaking apparatus (Heidolph Company). The solution was examined using the methods described in examples 2 and 3.

TABLE 5a

Composition of the formulations

|  | Formulation 8 | Formulation 9 |
| --- | --- | --- |
| G-CSF | 0.350 mg | 0.250 mg |
| Tween 80 | 0.1 mg | — |
| Tween 20 | — | 0.1 mg |
| Human serum albumin | — | 1 mg |
| Mannitol | 50 mg | 50 mg |
| Phosphate buffer | 5 mmol/l | 5 mmol/l |
| pH | 4.5 | 6.5 |
| Water for injection purposes | up to 1 ml | up to 1 ml |

TABLE 5b

Analytical results (Western blot)

|  | Formulation 5 | Formulation 6 |
| --- | --- | --- |
| without mechanical stress | 0.8% dimers no aggregates | 1.1% dimers no aggregates |
| after mechanical stress | 1.1% dimers no aggregates | 2.7% dimers 6.9% aggregates |

The results given in the table show that even the addition of human serum albumin cannot prevent aggregation and dimerization of the protein at pH 6.5 caused by mechanical stress. In contrast a solution which is stable towards mechanical stress is obtained at a pH value of 4.5 even when no human serum albumin is present as a stabilizing agent.

EXAMPLE 9

Long-Term Stability

A G-CSF injection solution was prepared by dissolving 0.35 mg/ml G-CSF in a solution of 50 mg/ml mannitol, 0.1 mg/ml polysorbate 80 and 0.5 mg phosphoric acid and adjusted to pH 4.5 with sodium hydrogen phosphate while stirring. The preparation and dispensing of the solution was carried out under a nitrogen atmosphere. The clear solution was sterilized by filtration using a sterilized membrane filter with a pore size of 0.2 μm, subsequently dispensed into injection bottles of hydrolytic class I and closed with suitable rubber stoppers. The pharmaceutical preparations containing G-CSF were stored for 9 months at temperatures of +4 to +8 and +20 to +25° C.

TABLE 6

Long-term stability at 4–8° C.

|  | 3 Months | 6 Months | 9 Months |
| --- | --- | --- | --- |
| biol. Activity 80%–125% | corresp. | corresp. | corresp. |

TABLE 6-continued

Long-term stability at 4–8° C.

|  | 3 Months | 6 Months | 9 Months |
|---|---|---|---|
| Western blot |  |  |  |
| % aggregates | n.d. | n.d. | n.d. |
| % dimers | <1% | <1% | <1% |
| SDS page % secondary peaks | <1% | <1% | <1% |
| RP-HPLC product peak | >99% | >99% | >99% |
| SEC HPLC |  |  |  |
| product peak | >98% | >98% | >98% |
| secondary peaks | <1% | <1% | <1% |
| turbidity TU/F | 0.7 | 0.7 | 0.7 |
| OD 280 | 0.359 | 0.362 | 0.357 |

EXAMPLE 10

G-CSF solutions having a concentration of ca. 5 mg/ml were diluted to a content of active substance of 0.35 mg/ml using the buffer solutions described in the following. All buffer solutions contained 0.05% polysorbate 80. The buffer solutions were prepared by adding arginine in the stated molar amount between 5 and 80 mmol/l and adjusting the pH value with phosphoric acid or hydrochloric acid or citric acid. The G-CSF buffer solutions obtained in this way were dispensed in amounts of 10 ml into injection bottles made of glass of hydrolytic class I, closed with suitable stoppers and shaken for 10 seconds at maximum intensity on a laboratory shaking apparatus (e.g. Heidolph Co.). After a standing time of ca. 10 minutes a turbidity value (TU/F) calibrated against a formazine standard (German Pharmacopeia) was determined with a LTP 5 scattered light photometer (measuring angle 90°) of the Dr. Lange Company.

The mean turbidity values of the unshaken and shaken solutions are shown in Table 7. The various molar concentrations (5, 10, 20, 40, 80 mmol) of arginine buffer systems lead to the same results in each case.

It was found that arginine buffer in a pH range of 7.0–7.5 acts particularly well against mechanical stress. Arginine buffers can be used particularly advantageously in solutions which were prepared by dissolving lyophilisates.

TABLE 7

Turbidity values using arginine buffers

| Buffer | Arginine/ Phosphoric acid | Arginine/ Hydrochloric acid | Arginine/ Citric acid |
|---|---|---|---|
| pH 7.5 | 0.40 | 0.42 | 0.51 |
| pH 7.0 unshaken | 0.43 | 0.54 | 0.76 |
| pH 7.5 | 0.49 | 0.62 | 0.53 |
| pH 7.0 shaken | 0.58 | 0.69 | 0.84 |

Average molarity 5–80 mmol/l

We claim:

1. A stable aqueous pharmaceutical preparation, comprising (i) a therapeutically effective amount of G-CSF, (ii) a buffer substance selected from the group consisting of citrate, maleate, a combination of phosphate and citrate, and arginine, or a salt thereof, selected from the group consisting of arginine phosphate, arginine chloride and arginine citrate and (iii) at least one surfactant in an amount less than the amount of G-CSF in the preparation, wherein the pH value of the preparation is between about 7 and 8, and the preparation is free of polymers or protein-like auxiliary substances or additives.

2. The preparation of claim 1, comprising an amount of surfactant which is at most 0.5 mg/ml.

3. The preparation of claim 2, wherein the amount is 0.01 to 0.1 mg/ml.

4. The preparation of claim 1, further comprising an additional member selected from the group consisting of an antioxidant, a chaotropic agent, an amino acid and an isotonizing agent.

5. A lyophilisate or powder of the preparation of claim 1.

6. An aqueous solution produced by dissolving the lyophilisate or powder of claim 5 in water.

7. A process for preparing a stable aqueous pharmaceutical preparation, comprising forming an aqueous solution comprising (i) a therapeutically effective amount of G-CSF, (ii) a buffer substance selected from the group consisting of citrate, maleate, a combination of phosphate and citrate, and arginine, or a salt thereof, selected from the group consisting of arginine phosphate, arginine chloride and arginine citrate and (iii) at least one surfactant in an amount less than the amount of G-CSF in the preparation, wherein the pH value of the preparation is between about 7 and 8.

8. A process for stabilizing an aqueous pharmaceutical preparation containing G-CSF, said process comprising adding to the preparation (i) a buffer substance selected from the group consisting of citrate, maleate, a combination of phosphate and citrate, and arginine, or a salt thereof, selected from the group consisting of arginine phosphate, arginine chloride and arginine citrate and (ii) at least one surfactant in an amount less than the amount of G-CSF in the preparation, wherein the pH value of the preparation is between about 7 and 8.

* * * * *